United States Patent [19]

Kawata

[11] Patent Number: 5,380,201
[45] Date of Patent: Jan. 10, 1995

[54] DENTAL HANDPIECE HAVING CLEANING UNIT

[75] Inventor: Sosaku Kawata, Kanuma, Japan

[73] Assignee: Nakanishi Dental Mfg. Co., Ltd., Japan

[21] Appl. No.: 134,319

[22] Filed: Oct. 6, 1993

[30] Foreign Application Priority Data

Oct. 9, 1992 [JP] Japan ............... 4-070613[U]

[51] Int. Cl.⁶ ..................................... A61C 1/05
[52] U.S. Cl. ............................. 433/132; 433/114
[58] Field of Search .............. 433/88, 84, 85, 132, 433/104, 114

[56] References Cited

U.S. PATENT DOCUMENTS 3,364,576  1/1968  Kern, Jr. .................... 433/132
4,941,828  7/1990  Kimura ....................... 433/132
4,978,297 12/1990  Vlock ......................... 433/126

Primary Examiner—Cary E. O'Connor
Attorney, Agent, or Firm—Malcolm B. Wittenberg

[57] ABSTRACT

A dental handpiece having a cleaning unit contains a turbine gas supply passage for supplying a gas under pressure to a turbine for rotationally driving a dental tool, a rinsing liquid supply passage for supplying a rinsing liquid to a turbine head, a chip-scattering gas supply passage for supplying a gas for scattering cut chips produced by operation of the dental tool, and a cleaning unit for cleaning at least one of the gas and the liquid provided in at least one of the turbine gas supply passage the rinsing liquid supply passage and the chip-scattering gas supply passage.

2 Claims, 2 Drawing Sheets

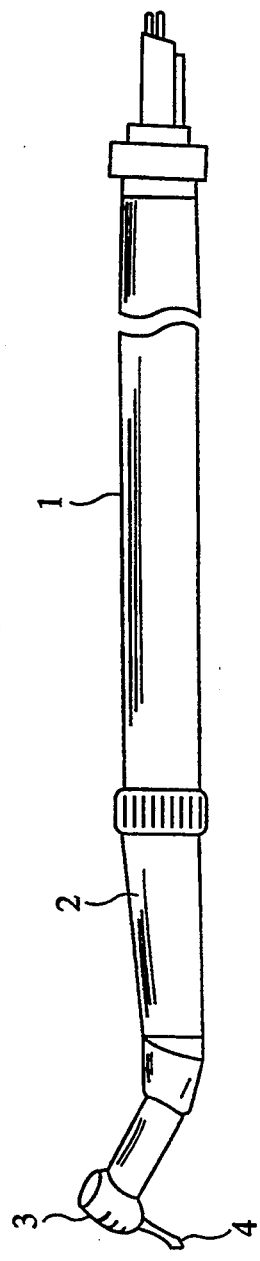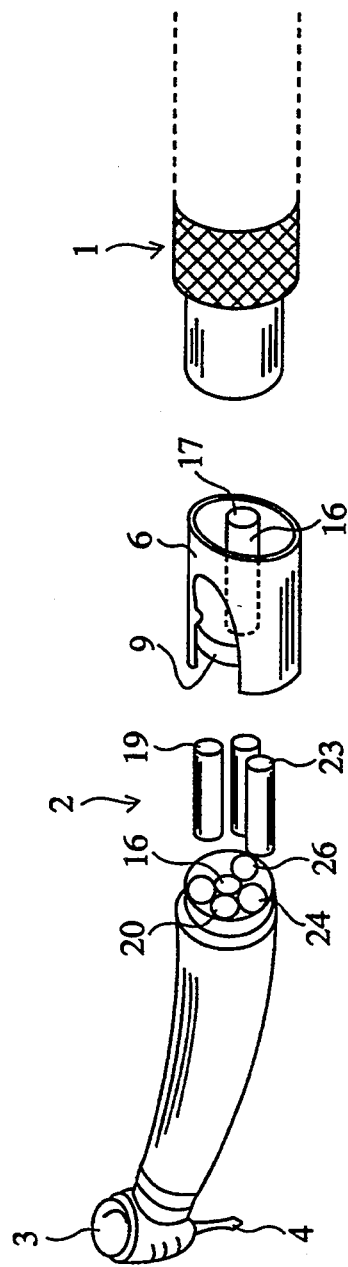

DENTAL HANDPIECE HAVING CLEANING UNIT

BACKGROUND OF THE INVENTION

This invention relates to a dental handpiece having a cleaning unit for causing clean gas or liquid to be passed through a gas supply passage for a turbine, a liquid supply passage for rising liquid or a chip-scattering gas supply passage for enabling the dental treatment to be performed under hygienic conditions.

There has hitherto been employed for dental treatment a dental handpiece fitted with a dental grinding tool, such as a bur, a point or a disc, for grinding or polishing teeth. The dental handpiece has a driving device, such as a turbine blade adapted for being rotated under air pressure in the inside of a turbine head. The dental handpiece also has an air supply passage for supplying air under pressure, a water passage for the rinsing water for rinsing teeth and a chip-scattering air supply passage for supplying air to scatter off cut chips or tooth debris on the downstream side of the turbine head. The driving device is adapted for driving a tooth cutting implement fitted with a cutting end. For dental treatment, such tooth cutting implement is selected which has a cutting end of a pre-set shape and size suited to the position or shape of the site of treatment or the object of treatment, and is exchangeably mounted at a tool head part of the turbine head.

However, with the above-described conventional dental handpiece, since air in a treatment room or tap water is directly introduced into the air supply passage for a turbine, the chip-scattering air supply passage or into the rinsing water supply passage and thence into the oral cavity of a patient, dental treatment cannot be performed under hygienic conditions if water or air or the inside of the piping connecting to the passages is contaminated.

On the other hand, with the dental handpiece in which when the supply of water under pressure during dental treatment is to be discontinued, the water under pressure is temporally sucked by e.g. a pull-back control valve to prevent dripping of the water, so that the water used for rinsing the oral cavity of the patient tends to flow back into the air discharge passage or the water supply passage to contaminate the inside of the piping.

SUMMARY OF THE INVENTION

It is a principal object of the present invention to provide a dental handpiece having a cleaning unit whereby clean gas or liquid maybe supplied to the foremost part of the dental handpiece to enable dental treatment to be performed under hygienic conditions.

It is another object of the present invention to provide a dental handpiece having a cleaning unit whereby impurities such as saliva, used rinsing water or tooth chips or debris occasionally sucked from the foremost part of the handpiece may be prevented from being propagated into the piping system.

It is yet another object of the present invention to provide a dental handpiece having a cleaning unit whereby a clean gas may be supplied to a turbine head to prevent the occurrence of troubles in the turbine head rotation due to solid substances such as dust and dirt.

The above and other objects of the present invention will become more apparent from the following description.

According to the present invention, there is provided a dental handpiece having a cleaning unit comprising a turbine gas supply passage for supplying a gas under pressure to a turbine for rotationally driving a dental tool, a rinsing liquid supply passage for supplying a rinsing liquid to a turbine head, a chip-scattering gas supply passage for supplying a gas for scattering cut chips produced by the operation of the dental tool, and cleaning means for cleaning the gas or the liquid provided in at least one of the turbine gas supply passage, the rinsing liquid supply passage and the chip-scattering gas supply passage.

BRIEF DESCRIPTION OF THE DRAWINGS

FIG. 1 is a side view showing a dental handpiece according to the present invention in its entirety.

FIG. 3 is an exploded perspective view of the dental handpiece shown in FIG. 1.

PREFERRED EMBODIMENTS OF THE INVENTION

Figure 2:
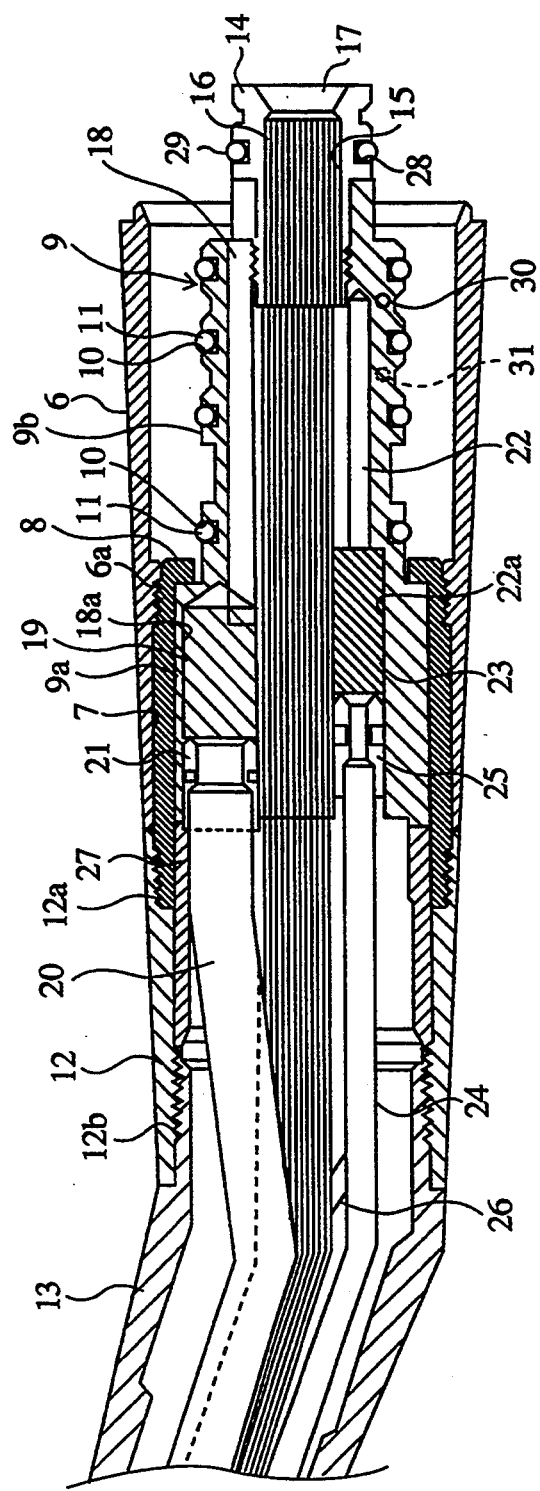
FIG. 2 is a partial cross-sectional view of the dental handpiece shown in FIG. 1.

Referring to the drawings, a preferred embodiment of the present invention will be explained in detail. In FIG. 1 showing the dental handpiece in its entirety, an air supply pipe, an air discharge pipe, a water supply pipe and an electric wire for a lamp are lead out at the rear end of a handpiece handle part 1. A handpiece mid part 2 is connected to the handpiece handle part 1. Within a turbine head 3 connected to the handpiece mid part 2, there is mounted a turbine blade, not shown, which is adapted for being rotated under air pressure in a well-known manner for driving a detachably mounted dental tool 4.

Referring to FIGS. 2 and 3, the handpiece mid part 2 is shown. A connecting tube 6 is fitted over the outer periphery of an end portion of the handpiece handle part 1. A tubular joint 7 is threadedly engaged with the inner surface of the connecting tube 6 by internal threads 6a and is formed with an inwardly directed rear flange 8.

A detachable turbine-side joint 9 is a transparent tubular member having its large-diameter base part 9a fitted into the inside of the tubular joint 7. The outer periphery of a reduced-diameter rear part 9b of the turbine-side joint 9 is formed with a plurality of ring-shaped grooves 10 for receiving seal rings 11 for forming channels for air or water therebetween in cooperation with the foremost insertable member of the handpiece handle part 1 when the handle part 1 is coupled to the mid part 2. A sleeve 12 is threadedly engaged with the foremost part of the tubular joint 7 protruded beyond the foremost part of the connecting tube 6 for securing the turbine-side joint 9 against incidental extraction from the joint 7 via a collar 27 previously fitted in position on the inner periphery of the tubular joint 7. The inner periphery of the sleeve 12 is threadedly engaged with a head shaft part 13 by internal threads 12b formed in the sleeve 12. The turbine head 3 ia carried at the foremost part of the head shaft part 13.

An optical fiber member holding tube 14 having a seal ring 29 fitted in an annular outer peripheral groove 28 thereof is threadedly engaged with the rear end of the turbine-side joint 9. An optical fiber member 16 having its one end held by the holding tube 14 is introduced into the inside of the turbine head 3 via a bore 15 in the turbine-side joint 9 and the head shaft part 13. A conically-shaped light collecting member 17 is fitted at the rear end part of the holding tube 14 at some distance from a lamp, not shown, provided within the handpiece handle part 1 when fitted in the connecting tube 6 so as to cause light from the lamp to fall on the rear end face of the optical fiber member 16.

Within the turbine-side joint 9 is an air supply bore 18 as an air supply channel. Within a large diameter portion 18a of the bore 18 is mounted an end of an air supply pipe 20 constituting a portion of a turbine driving air supply channel via an air supply filter 19 and a seal connector 21. The filter 19 is formed of a porous material which is permeable to air but is not permeable to water, such as polytetrafluoroethylene. The air supply pipe 20 is extended from within the head shaft 13 as far as a turbine, not shown, within the turbine head 3. The air returned from the turbine after running the turbine in rotation is led via an exhaust pipe, not shown, provided side by side with the air supply pipe 20 to an air exhaust port, also not shown, formed within the turbine-side joint 9.

A water supply bore 22 as a water supply channel is formed within the turbine-side joint 9 and has a large-diameter portion 22a in which there is mounted an end of a water supply pipe 24 constituting a portion of the water supply channel via a seal connector 25 and a water supply filter 23. The water supply pipe 24 is connected via an inside of the head shaft 13 to an ejection port, not shown, of the turbine head 3. A chip-scattering air supply bore, not shown, is provided as a chip-scattering air supply channel on the reverse side with respect to the water supply bore 22. A chip-scattering air supply pipe 26 (FIG. 2) constituting a portion of the chip-scattering air supply channel is connected to the chip-scattering air supply bore, via an air supply filter 19. The water supply pipe 24 and the air supply pipe 26 are led towards the turbine head 3.

The turbine-side joint 9 has a water supply port 30 and an air supply port 31 connecting the water supply bore 22 and the chip-scattering air supply bore to the surfaces of the grooves 10 between the seal rings 11, respectively. When the handpiece handle part 1 is connected to the handpiece mid part 2, the end of the air supply bore 18 disposed between the seal rings 11 and 29 is connected to an air supply pipe, not shown, provided in the handpiece handle part 1, while the air exhaust port in the turbine-side joint 9 is connected to an air exhaust pipe, also not shown, provided in the handpiece handle part 1. Similarly, the water supply port 30 between the seal rings 11 is connected to a water supply pipe, not shown, of the handpiece handle part 1, while the air supply port 31 between the seal rings 11 is connected to a chip-scattering air supply pipe, not shown, of the handpiece handle part 1.

Air under compression is supplied to the air supply bore 18 and thence transmitted via the filter 19 and the air supply pipe 20 to the turbine blade for running the turbine blade in rotation. The air from the turbine blade is transmitted via the air exhaust port, not shown, towards the air discharge pipe of the handpiece handle part 1. The solid matter such as dust and dirt contained in air in the treatment room may be removed by the filter 19 before the air is drawn into the oral cavity so that dental treatment may be carried out under hygienic conditions.

The rinsing water introduced via the water supply port 30 into the water supply bore 22 is passed through the filter 23 so as to be freed of contaminants or bacteria before being poured onto the teeth. The chip scattering air is similarly guided through the chip scattering air pipe 26 via the filter 19 so as to be ejected on the teeth for instantly scattering the cut chips to outside by the compressed unpolluted and bacteria-free air.

The filters 19, 23 act for removing the dust and dirt, solid matter, contaminants or bacteria contained in air and water, so that clean air or water may be perpetually supplied into the oral cavity. In addition, rinsing water, saliva, or cut, chips reversed from the foremost part of the turbine head upon cessation of supply of air or water may be cleaned. The turbine-side joint 9 is formed of a transparent material and hence the contaminated state of the filters may be checked from outside by detaching the sleeve 12 from the tubular joint 7 and dismounting the sleeve 12 along with the collar 27 so that the contaminated filters may be exchanged with new ones. The dental handpiece may be improved in durability because there is no risk of the turbine bearings being broken by the contaminants carried by air.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece having a cleaning unit comprising a turbine gas supply passage for supplying a gas under pressure to a turbine for rotationally driving a dental tool, a rinsing liquid supply passage for supplying a rinsing liquid to a turbine head, a chip-scattering gas supply passage for supplying a gas for scattering cut chips produced by operation of said dental tool, cleaning means for cleaning at least one of the gas and the liquid provided in at least one of said turbine gas supply passage, said rinsing liquid supply passage and said chip-scattering gas supply passage, and a gas exhaust passage for discharging the gas under pressure to outside after having run the turbine in rotation, said cleaning means being provided in said gas exhaust passage, said cleaning means comprising a filter and a transparent member for securing said filter.

2. A dental handpiece having a cleaning unit comprising a turbine gas supply passage for supplying a gas under pressure to a turbine for rotationally driving a dental tool, a rinsing liquid supply passage for supplying a rinsing liquid to a turbine head, a chip-scattering gas supply passage for supplying a gas for scattering cut chips produced by operation of said dental tool, cleaning means for cleaning at least one of the gas and the liquid provided in at least one of said turbine gas supply passage, said rinsing liquid supply passage and said chip-scattering gas supply passage, said cleaning means comprising a filter and a transparent member for securing said filter.

* * * * *